(12) United States Patent
Makino et al.

(10) Patent No.: US 12,352,743 B2
(45) Date of Patent: Jul. 8, 2025

(54) TENSION MEASURING DEVICE

(71) Applicant: NIHON KOHDEN CORPORATION, Tokyo (JP)

(72) Inventors: Hodaka Makino, Tokorozawa (JP); Tetsuya Ogawa, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 753 days.

(21) Appl. No.: 17/194,682

(22) Filed: Mar. 8, 2021

(65) Prior Publication Data
US 2021/0285935 A1    Sep. 16, 2021

(30) Foreign Application Priority Data

Mar. 16, 2020    (JP) ................ 2020-045693

(51) Int. Cl.
*G01N 33/50*    (2006.01)
*G01N 33/483*    (2006.01)

(52) U.S. Cl.
CPC ....... *G01N 33/5061* (2013.01); *G01N 33/483* (2013.01)

(58) Field of Classification Search
CPC . G01N 33/5061; G01N 33/483; C12M 41/00; C12M 21/08; C12M 35/04
See application file for complete search history.

(56) References Cited

U.S. PATENT DOCUMENTS

| | | | |
|---|---|---|---|
| 4,911,713 A | 3/1990 | Sauvage et al. | |
| 5,081,035 A * | 1/1992 | Halberstadt | C12M 23/24 |
| | | | 210/321.79 |
| 5,284,766 A | 2/1994 | Okano et al. | |
| 5,792,603 A | 8/1998 | Dunkelman et al. | |
| 5,846,828 A | 12/1998 | Peterson et al. | |
| 6,060,306 A | 5/2000 | Flatt et al. | |
| 6,121,042 A | 9/2000 | Peterson et al. | |
| 2001/0043918 A1 | 11/2001 | Masini et al. | |
| 2004/0219659 A1 * | 11/2004 | Altman | C12M 29/10 |
| | | | 435/284.1 |

(Continued)

FOREIGN PATENT DOCUMENTS

| | | |
|---|---|---|
| EP | 3 477 302 A1 | 5/2019 |
| JP | 2-211865 A | 8/1990 |

(Continued)

OTHER PUBLICATIONS

Haraguchi, Yuji et al., "Scaffold-free tissue engineering using cell sheet technology", RSC Advances, 2012, vol. 2, pp. 2184-2190. (7 pages total).

(Continued)

*Primary Examiner* — Liban M Hassan
(74) *Attorney, Agent, or Firm* — Sughrue Mion, PLLC (57) ABSTRACT

A tension measuring device include a first container in which a cell structure is disposed and which is charged with a culture medium so that the cell structure is immersed therein; a second container in which a medical agent to be given to the inside of the first container is injected; a first tube which links the first container and the second container liquidtightly; and a pump which is disposed over the first tube and causes liquid to flow into the first container from the second container.

11 Claims, 7 Drawing Sheets

(56) References Cited

U.S. PATENT DOCUMENTS

| | | | |
|---|---|---|---|
| 2005/0176140 A1* | 8/2005 | Benedict | C12M 27/02 435/366 |
| 2006/0194193 A1 | 8/2006 | Tsuruta et al. | |
| 2009/0181448 A1 | 7/2009 | Fan et al. | |
| 2011/0117645 A1 | 5/2011 | Yasuda et al. | |
| 2012/0184024 A1* | 7/2012 | Steen | A01N 1/0247 435/284.1 |
| 2013/0109012 A1 | 5/2013 | Sniadecki et al. | |
| 2014/0127756 A1* | 5/2014 | Bolz | C12M 27/20 366/315 |
| 2019/0120742 A1* | 4/2019 | Kubo | A61B 5/4519 |
| 2020/0278342 A1 | 9/2020 | Kubo et al. | |

FOREIGN PATENT DOCUMENTS

| | | |
|---|---|---|
| JP | 2002-500004 A | 1/2002 |
| JP | 2006-174828 A | 7/2006 |
| JP | 2009-136797 A | 6/2009 |
| JP | 2019-76046 A | 5/2019 |
| JP | 2020-10683 A | 1/2020 |
| JP | 2020-141661 A | 9/2020 |
| TW | M504092 U * | 7/2015 |
| WO | 2009/123349 A1 | 10/2009 |

OTHER PUBLICATIONS

Zhao, Yimu et al., "A Platform for Generation of Chamber-Specific Cardiac Tissues and Disease Modeling", Cell, Feb. 7, 2019, vol. 176, pp. 1-15. (34 pages total).

Matsuura, Katsuhisa et al., "Creation of human cardiac cell sheets using pluripotent stem cells", Biochemical and Biophysical Research Communications, vol. 425, 2012, pp. 321-327. (7 p. total).

Extended European Search Report dated Jul. 16, 2021, issued by the European Patent Office in counterpart European patent Application No. 21161235.3.

Matsuura, Katsuhisa et al., "Creation of human cardiac cell sheets using pluripotent stem cells", Biochemical and Biophysical Research Communications, vol. 425, 2012, pp. 321-327. (7 pages total).

Office Action issued on Jan. 30, 2024 by the Japanese Patent Office in corresponding JP Patent Application No. 2020-045693.

Communication issued on Jul. 2, 2024 by the Japanese Patent Office for Japanese Patent Application No. 2020-045693.

* cited by examiner

TENSION MEASURING DEVICE

CROSS-REFERENCE TO RELATED APPLICATIONS

The present application claims priority from Japanese Patent Application No. 2020-045693, filed Mar. 16, 2020, the entire content of which is incorporated herein by reference.

TECHNICAL FIELD

The presently disclosed subject matter relates to a tension measuring device for a cell structure including muscle cells.

BACKGROUND ART

In recent years, drug discovery screening methods utilizing pluripotent stem cells, such as iPS cells, having an ability to be differentiated into various kinds of functional cells have been being developed. However, conventional evaluation systems use cells themselves and do not reflect a state of a biological tissue. It is therefore desired to develop an evaluation system for simulating a biological tissue from somatic cells derived from pluripotent stem cells through differentiation.

For example, a method of sowing cells on a three-dimensional structure called a scaffold, a method of decellularizing an organ or tissue and sowing cells on a remaining matrix to form a three-dimensional structure, and a method of stacking, three-dimensionally, cell sheets produced by peeling into sheet form have been developed as attempts for constructing cells in a three-dimensional manner (refer to Patent document JP-A-02-211865 and Non-patent document Haraguchi Y. et al., "Scaffold-free Tissue Engineering Using Cell Sheet Technology," RSC Adv., 2012; 2: 2184-2190, for example).

Research and development of evaluation systems to be used for drug discovery screening are being performed by making full use of the above techniques. In this connection, Patent document JP-A-2019-76046 below discloses a tension measuring device, system, and kit for a sheet-like tissue including myocardial cells.

The tension measuring device of Patent document JP-A-2019-76046 is equipped with a high-sensitivity tension detecting means for measuring a very weak tension originating from pulsations of myocardial cells. Furthermore, in the tension measuring device of Patent document JP-A-2019-76046, a medical agent flows directly into a culture medium tank (first container) in which myocardial cells are disposed. As a result, the tension detecting means may not be able to measure tension accurately because vibration that occurs in association with inflow of the medical agent affects the tension detecting means.

SUMMARY OF INVENTION

The presently disclosed subject matter has been conceived to solve the above problem, and has as an object providing a tension measuring device capable of measuring tension accurately by reducing vibration that affects a tension detecting means.

A tension measuring device according to the presently disclosed subject matter that attains the above object is a tension measuring device for a cell structure including muscle cells. The tension measuring device includes a first container in which the cell structure is disposed and which is charged with a culture medium so that the cell structure is immersed therein; a second container in which a medical agent to be given to the inside of the first container is injected; a first tube which links the first container and the second container liquidtightly; and a pump which is disposed over the first tube and causes liquid to flow into the first container from the second container.

In the above-described tension measuring device, liquid and culture medium flows into the first container from the second container through the first tube 60 by the pump 70. Thus, vibration that affects a tension detecting means can be made weaker than in a case that the medical agent is caused to flow into the first container directly. As a result, a tension measuring device can be provided that can measure tension accurately by reducing vibration that affects a tension detecting means.

DESCRIPTION OF EMBODIMENTS

Embodiment 1

A first embodiment of the presently disclosed subject matter will be hereinafter described with reference to the accompanying drawings. In the descriptions of the drawings, the same constituent elements will be given the same symbol and will not be described redundantly. Ratios between dimensions in the drawings may be exaggerated for convenience of description and hence be different from actual ratios.

Figure 1:
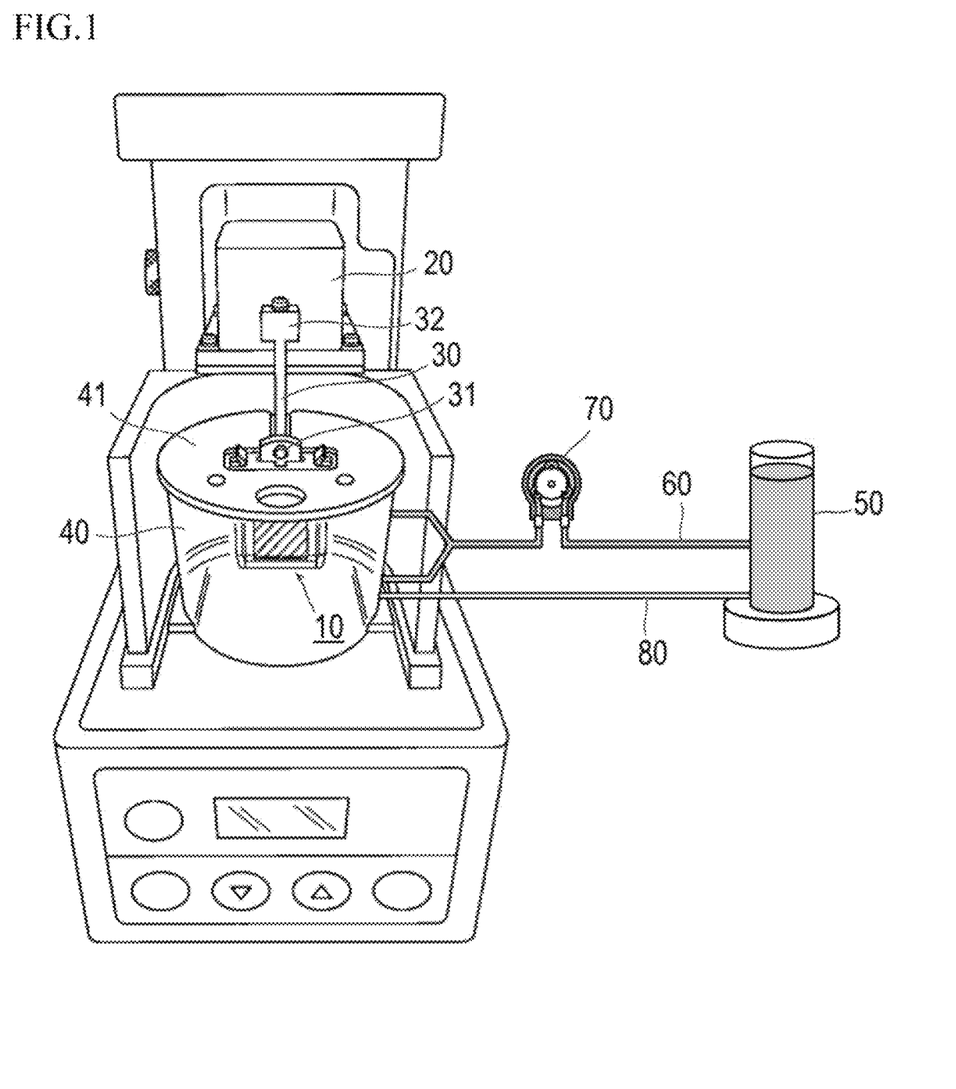
FIG. 1 is a rough perspective view of a tension measuring device according to a first embodiment of the presently disclosed subject matter.
Figure 2:
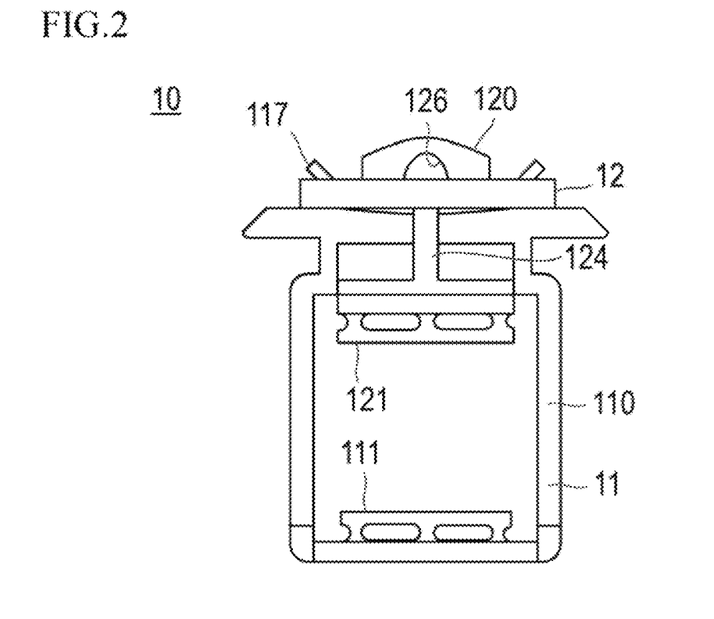
FIG. 2 is a schematic diagram illustrating a gel adaptor holder assembly.
Figure 3:
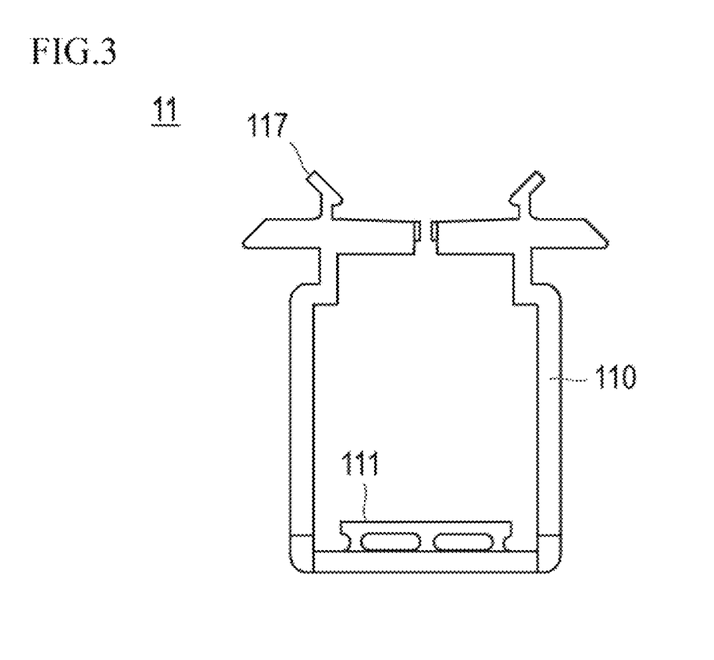
FIG. 3 is a schematic diagram illustrating a first gel adaptor holder.
Figure 4:
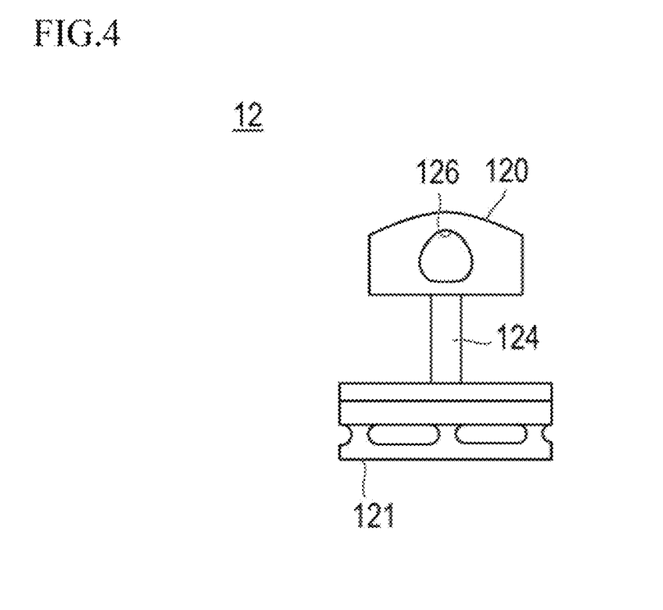
FIG. 4 is a second schematic diagram illustrating a second gel adaptor holder.
Figure 5A:
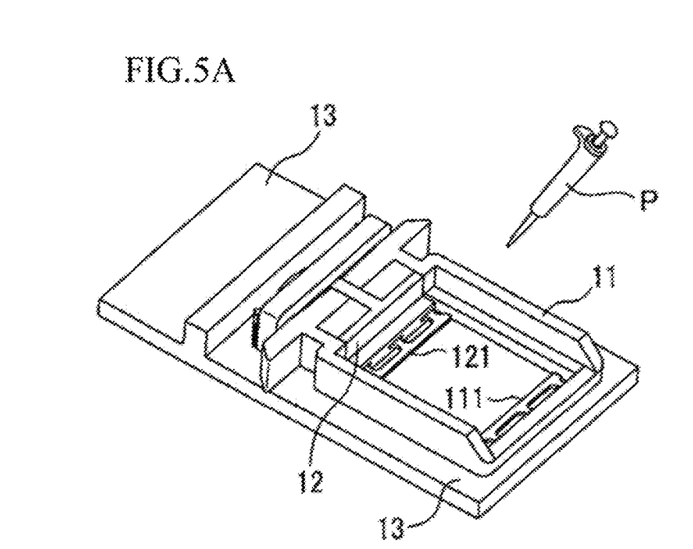
FIG. 5A is diagrams for description of a method for setting a gel and a cell structure in the first gel adaptor holder and the second gel adaptor holder.

FIG. 1 is a rough perspective view of a tension measuring device 1 according to the first embodiment of the presently disclosed subject matter. FIG. 2 is a schematic diagram illustrating a gel adaptor holder assembly 10. FIG. 3 is a schematic diagram illustrating a first gel adaptor holder 11. FIG. 4 is a second schematic diagram illustrating a second gel adaptor holder 12. FIG. 5A to SD is diagrams for description of a method for setting a gel G and a cell structure CS in the first gel adaptor holder 11 and the second gel adaptor holder 12. FIG. 6 is a schematic diagram illustrating part of the tension measuring device 1 according to the first embodiment.

Before describing the configuration of the tension measuring device 1 according to this embodiment, a description will be made of a cell structure CS including muscle cells that is a target of measurement of the tension measuring device 1.

<Cell Structure Including Muscle Cells>

In this specification, the term "cell structure including muscle cells" means a biological tissue including muscle cells (e.g., myocardial tissue, skeletal muscle tissue, smooth muscle tissue) taken from a living body or a structure including muscle cells. The cell structure including muscle cells that can be used in the presently disclosed subject matter may be either a biological tissue itself taken from a living body or a biological tissue obtained by treating a biological tissue taken from a living body such as a myocardial tissue using myocardial cells originating from human iPS cells. Furthermore, the cell structure including muscle cells that can be used in the presently disclosed subject matter may be a cell structure formed by mixing a suspension including muscle cells and a gel solution or a gelling agent or a cell sheet. Still further, the cell structure including muscle cells that can be used in the presently disclosed subject matter may be a cell structure formed by sowing cell groups including muscle cells on a gel and culturing them.

In one mode of practice, the cell structure including muscle cells that can be used in the presently disclosed subject matter may be a cell structure may be at least one selected from the group consisting of a sheet-like cell structure, a rod-like cell structure, and a string-like cell structure, among which a sheet-like cell structure is preferable.

In this specification, the term "sheet-like cell structure" means a film-like cell structure having an average thickness that is, for example, larger than or equal to about 10 μm (e.g., a thickness of one cell) and smaller than or equal to about 2 mm and having such a length as to be able to be used between a first gel holding portion and a second gel holding portion described later). There are no limitations on the width of the "sheet-like cell structure" except that it should be able to be used with the first gel holding portion and the second gel holding portion. Either a single "sheet-like cell structure" or plural "sheet-like cell structures" may be used for the tension measuring device. The plural "sheet-like cell structures" may be used in such a manner as to be either arranged parallel with each other between the first gel holding portion and the second gel holding portion or stacked on each other.

In this specification, the term "rod-like cell structure" means a cell structure having an average diameter that is, for example, larger than or equal to about 100 μm and smaller than or equal to about 5 mm and having such a length as to be able to be used between the first gel holding portion and the second gel holding portion described later). Either a single "rod-like cell structure" or plural "rod-like cell structures" may be used for the tension measuring device. The plural "rod-like cell structures" may be used in such a manner as to be either arranged parallel with each other between the first gel holding portion and the second gel holding portion or bundled together.

In this specification, the term "string-like cell structure" means a three-dimensional cell structure having an average diameter that is, for example, larger than or equal to about 10 μm and smaller than or equal to about 100 μm and having such a length as to be able to be used between the first gel holding portion and the second gel holding portion described later). Either a single "string-like cell structure" or plural "string-like cell structures" may be used for the tension measuring device. The plural "string-like cell structures" may be used in such a manner as to be either arranged parallel with each other between the first gel holding portion and the second gel holding portion or bundled together.

Although the different terms "rod-like cell structure" and "string-like cell structure" are used above for convenience depending on the diameter, they both mean a long and narrow cell structure and may be used interchangeably.

For example, the "rod-like cell structure" or the "string-like cell structure" that can be used in the presently disclosed subject matter may be formed by either shaping (e.g., taking up, twisting, contracting, or cutting) a sheet-like cell structure into a rod shape or a string shape or causing a suspension containing cells and a desired gel to flow into a rod-shaped or string-shaped mold (refer to Zhao Y., Cell. 2019 Feb. 7; 176(4): 913-927, for example).

In this specification, the term "cell structure including muscle cells" means a cell structure in which muscle cells account for at least 10% or more, for example, 15% or more, 20% or more, 25% or more, 30% or more, 35% or more, 40% or more, 45% or more, 50% or more, 55% or more, 60%/o or more, 65% or more, 70% or more, 75% or more, 80% or more, 85% or more, 90% or more, 95% or more, or 99% or more, of the cells included in the cell structure. In this specification, the term "muscle cells" means contractive cells that form an animal body muscle tissue, such as myocardial cells, skeletal muscle cells, and smooth muscle cells. In one mode of practice, the "muscle cells" used in the presently disclosed subject matter are cells of one kind selected from the group consisting of "myocardial cells, skeletal muscle cells, and smooth muscle cells. The muscle cells that can be used in the presently disclosed subject matter may be muscle cells originating from an animal, such as muscle cells of a mammal, a bird, an amphibian, a reptile, or a fish. It is preferable to use muscle cells originating from a mammal such as a mouse, a rat, a human, a monkey, a pig, a dog, a sheep, a cat, or a goat.

The muscle cells that can be used in the presently disclosed subject matter may be primary cells taken from a biological tissue, established cells, or cells derived from pluripotent stem cells or tissue stem cells through differentiation.

In this specification, the term "pluripotent stem cells" is intended to be a generic term of stem cells having an ability to be differentiated into cells of every tissue (pluripotency). The term "pluripotent stem cells" includes embryonic stem cells (ES cells), embryonic carcinoma cells (EC cells), trophoblast stem cells (TS cells), epiblast stem cells (EpiS cells), embryonic germ cells (EG cells), multipotent germ-line stem cells (mGS cells), induced pluripotent stem cells (iPS cells), and Muse cells (not restricted to them). ES cells and iPS cells are preferable. Known desired pluripotent stem cells can be used; for example, pluripotent stem cells disclosed in WO 2009/123349 (PCT/JP 2009/057041) can be used.

The muscle cells that can be used in the presently disclosed subject matter may be cells derived from pluripotent stem cells through differentiation. The method for differentiating pluripotent stem cells into muscle cells may be a known method (refer to Matsuura K. et al., "Creation of Human Cardiac Cell Sheets Using Pluripotent Stem Cells," Biochem. Biophys. Res. Commun. 2012 Aug. 24; 425(2): 321-327, for example).

The cell structure including muscle cells may include cells other than muscle cells. For example, the cell structure including muscle cells may include cardiac myoblasts, myoblasts, mesenchymal stem cells, vascular endothelial cells, endothelial progenitor cells, fibroblasts, or the like.

The cell structure CS including muscle cells has been described above. Next, the configuration of the tension measuring device 1 according to the embodiment will be described.

As shown in FIG. 1, the tension measuring device 1 can include the gel adaptor holder assembly 10 which is to hold a gel G and a cell structure CS, a tension detecting means 20 for detecting a tension that originates from pulsations of the cell structure CS, a link member 30 which links the gel adaptor holder assembly 10 and the tension detecting means 20, a first container 40 in which the cell structure CS and the gel adaptor holder assembly 10 are disposed, a second container 50 in which a medical agent to be given to the inside of the first container 40 is injected, a first tube 60 which links the first container 40 and the second container 50 liquidtightly, a pump 70 which is disposed over the first tube 60, and a second tube 80 which links the first container 40 and the second container 50 liquidtightly.

As shown in FIGS. 2-5, the gel adaptor holder assembly 10 holds the gel G and the cell structure CS.

A gel (1) to which a cell structure including muscle cells can be adhered, (2) that has such strength as to be able to keep a sheet shape, and (3) that does not adversely affect growth of cells, manifestation of their function, etc., that is, a biocompatible gel, can be used in the presently disclosed subject matter. For example, the gel that can be used in the presently disclosed subject matter is a hydrogel. Example hydrogels that can be used in the presently disclosed subject matter are hydrogels obtained by chemically crosslinking water-soluble, hydrophilic, or water-absorptive synthetic polymers such as polyacrylamide, polyacrylic acid, polyhydroxyethyl methacrylate, polyvinyl alcohol, polylactic acid, or polyglycolic acid, polysaccharides, proteins, nucleic acids, etc. Example polysaccharides are glycosaminoglycans such as hyaluronic acid and chondroitin sulfate, starch, glycogen, agarose, pectin, and cellulose. Example proteins are collagen and gelatin as its hydrolysate, proteoglycan, fibronectin, vitronectin, laminin, entactin, tenascin, thrombospondin, von Willebrand factor, osteopontin, and fibrinogen (e.g., a fibrin gel produced through reaction between fibrinogen and thrombin). Each of these hydrogels may be used after being increased in strength by being subjected to crosslinking treatment using a known method. The gel that can be used in the presently disclosed subject matter is preferably a fibrin gel. In one embodiment of the presently disclosed subject matter, the gel may be one formed in advance through mixing with cells.

Although an example configuration of the gel adaptor holder assembly 10 will be described below, the configuration of the gel adaptor holder assembly 10 is not limited to the following one except that it should be able to hold a gel G and a cell structure CS.

The gel adaptor holder assembly disclosed in Japanese Patent Application No. 2019-036677 can be used as the gel adaptor holder assembly 10. Thus, the gel adaptor holder assembly 10 will not be described in detail here and its configuration will be described only roughly.

As shown in FIGS. 2-4, the gel adaptor holder assembly 10 can include the first gel adaptor holder 11 and the second gel adaptor holder 12.

The first gel adaptor holder 11 and the second gel adaptor holder 12 constitute the gel adaptor holder assembly 10 when assembled as shown in FIG. 2.

As shown in FIGS. 2 and 3, the first gel adaptor holder 11 can include a frame member 110, a first gel holding portion 111 to which one end of a gel G is to be fixed, and a pair of nails 117 that are fixed to a lid 41 of the first container 40.

Equipped with the frame member 110, the gel adaptor holder assembly 10 can be attached to the lid 41 (described later) of the first container 40 with the shapes of the gel G and the cell structure CS kept as they are.

There are no particular limitations on the material of the first gel adaptor holder 11; example materials are polyethylene, polypropylene, polycarbonate, polystyrene, polyvinyl chloride, nylon, polyurethane, polyurea, polylactic acid, polyglycolic acid, polyvinyl alcohol, polyvinyl acetate, poly (metha)acrylic acid, poly(metha)acrylic acid derivatives, polyacrylonitrile, poly(metha)acrylamide, poly(metha)acrylamide derivatives, polysulfone, cellulose, cellulose derivatives, polysilicone, and metals.

As shown in FIGS. 2 and 4, the second gel adaptor holder 12 can include a connection portion 120 to which the link member 30 is linked, a second gel holding portion 121 to which the other end of the gel G is to be fixed, and a link portion 124 which links the connection portion 120 and the second gel holding portion 121.

The connection portion 120 is formed with a connection hole 126 for connection to the link member 30.

The material of the second gel adaptor holder 12 can be the same as that of the first gel adaptor holder 11.

In the following, a method for setting a gel G and a cell structure CS in the first gel adaptor holder 11 and the second gel adaptor holder 12 will be described with reference to FIG. 5A to 5D. The method disclosed in Japanese Patent Application No. 2019-036677 can be employed as this method. Thus, the method for setting a gel G and a cell structure CS will not be described in detail here and will be described only roughly.

First, the first gel adaptor holder 11 and the second gel adaptor holder 12 are set on a substrate 13 and a non-set gelling agent (e.g., a mixed liquid of fibrinogen (SIGMA, from bovine plasma, type 1-S), thrombin (SIGMA, from bovine plasma, T4648), a $CaCl_2$ solution (8 mM), and Factor XIII (CSL Behring, for intravenous injection of Fibrogamin P)) is injected using a pipette P (see FIG. 5A).

Figure 5B:
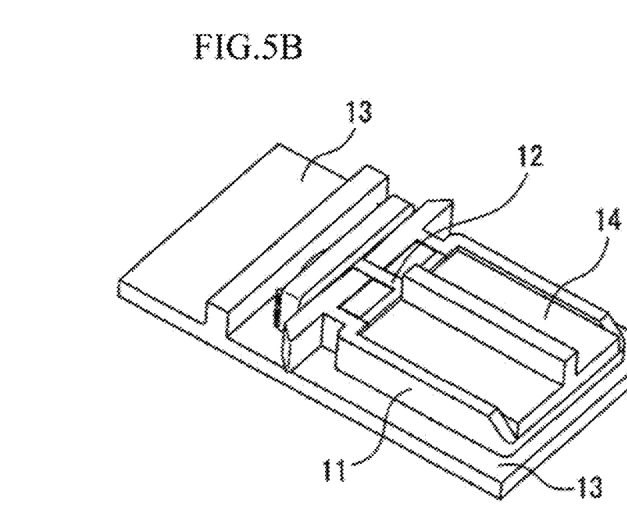
FIG. 5B is diagrams for description of a method for setting a gel and a cell structure in the first gel adaptor holder and the second gel adaptor holder.
Figure 6:
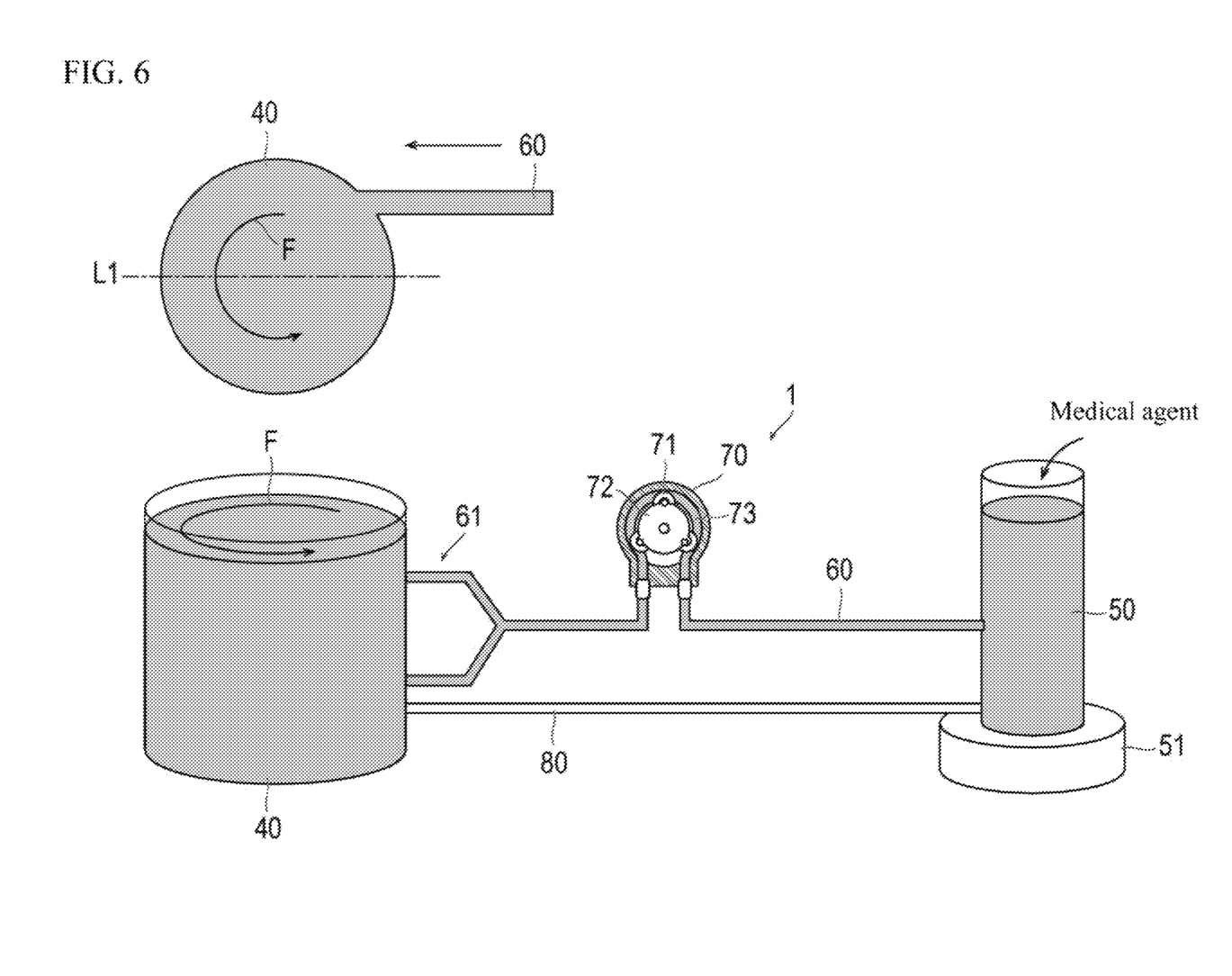
FIG. 6 is a schematic diagram illustrating part of a tension measuring device according to the first embodiment.

Then a gel forming lid 14 is put on the first gel holding portion 111 and the second gel holding portion 121 (FIG. 5B).

Figure 5C:
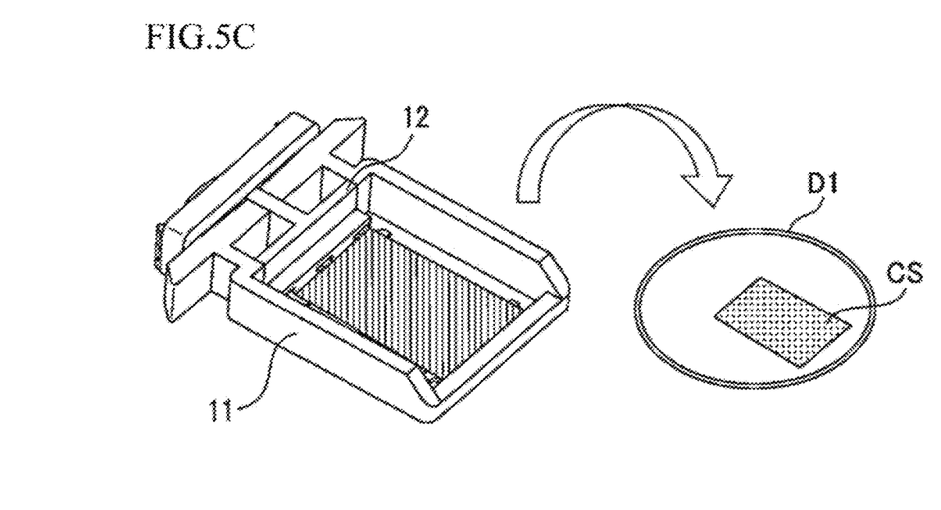
FIG. 5C is diagrams for description of a method for setting a gel and a cell structure in the first gel adaptor holder and the second gel adaptor holder.

After setting of the gel, the gel forming lid 14 and the substrate 13 are removed from the first gel adaptor holder 11 and the second gel adaptor holder 12 (see FIG. 5C).

Separately from the above work, in advance, cell groups including muscle cells are sown on a temperature-responsive culture dish DI (e.g., Ypcell (registered trademark; CellSeed Inc., Tokyo, Japan)) and cultured at 37° C. until they become confluent.

The first gel adaptor holder 11 and the second gel adaptor holder 12 having the gel produced above are then put on a cell structure CS including the muscle cells formed on the temperature-responsive culture dish DI (see FIG. 5C).

Figure 5D:
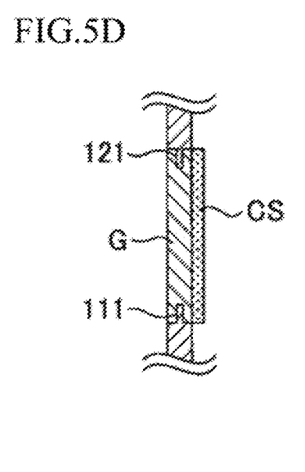
FIG. 5D is diagrams for description of a method for setting a gel and a cell structure in the first gel adaptor holder and the second gel adaptor holder.

Subsequently, while the temperature is kept lower than or equal to a lower critical solution temperature (e.g., 20° C.) of the temperature-responsive culture dish DI, the cell structure CS including the muscle cells is peeled off the temperature-responsive culture dish DI and, at the same time, adhered to the bottom surface of the gel G (see FIG. 5D).

A description of the rest of the configuration of the tension measuring device 1 will be made below.

The tension detecting means 20 measures tension that is produced by pulsations of the cell structure CS including the muscle cells. As shown in FIG. 1, the tension detecting means 20 is connected to the gel adaptor holder assembly 10 by the link member 30. When the cell structure CS including the muscle cells contracts, the second gel adaptor holder 12 is pulled downward in the vertical direction and a resulting load is measured by the tension detecting means 20 via the link member 30. For example, a known load cell can be used as the tension detecting means 20.

As shown in FIG. 1, the link member 30 links the gel adaptor holder assembly 10 and the tension detecting means 20. The link member 30 can include a hook 31 and a connection portion 32.

The hook 31 is inserted in the connection hole 126 of the second gel adaptor holder 12. The connection portion 32 is connected to the tension detecting means 20.

The structure of the link member 30 is not limited to the above-described structure as long as it can link the second gel adaptor holder 12 and the tension detecting means 20.

The gel adaptor holder assembly 10 having the gel G and the cell structure CS is housed in the first container 40. The lid 41 is attached to the first container 40.

The pair of nails 117 of the first gel adaptor holder 11 are fitted into the lid 41.

The second container 50 is configured so as to have approximately the same height as the first container 40 does. A medical agent to be given to the inside of the first container 40 is injected in the second container 50. The second container 50 has a smaller surface area than the first container 40. With this structure, the medical agent and a culture medium can be sent from the second container 50 to the first container 40 using small amounts of them. In the following description, the medical agent and/or the culture medium may be referred to as a "liquid."

As shown in FIG. 6, a heater 51 is disposed under the second container 50. If, for example, a heater were disposed under the first container 40, evaporation of culture medium would occur due to a local temperature increase. In contrast, in the embodiment, since the heater 51 is disposed under the second container 50, evaporation of culture medium due to a local temperature increase can be prevented. The configuration that a heater is disposed under the first container 40 is also included in the presently disclosed subject matter.

The first tube 60 links the first container 40 and the second container 50 liquidtightly. As shown in FIG. 6, the first tube 60 is connected to the first container 40 so as to be offset from a center line L1 that passes through the center of the first container 40 and is perpendicular to the first container 40 which extends in the vertical direction when viewed from above in the vertical direction. With this configuration, a rotational flow F is generated in the first container 40, whereby stirring is accelerated. Thus, the medical agent can be stirred with respect to the culture medium faster. Furthermore, an oxygen concentration gradient (the oxygen concentration is higher in a top portion of the first container 40) can be flattened.

As shown in FIG. 6, the first tube 60 branches into two tubes in the vertical direction at a position 61 where it is connected to the first container 40. With this structure, the medical agent can be mixed faster while the flow speed of liquid flowing into the first container 40 is lowered than with a structure that a single first tube 60 is connected to the first container 40 without branching into two tubes in the vertical direction.

As shown in FIG. 6, the pump 70 is disposed over the first tube 60. There are no particular limitations on the type of the pump 70; a tube pump 70 can be used. The use of the tube pump 70 as the pump 70 makes it possible to control the liquid movement from the second container 50 to the first container 40 easily.

As shown in FIG. 6, the tube pump 70 can include three rollers 71 which are arranged in the circumstantial direction at intervals of 120°, a rotary portion 72 for rotating the three rollers 71 in the circumstantial direction, and a tube 73 which is connected to the first tube 60.

The three rollers 71 of the tube pump 70 press the tube 73 as they are rotated in the circumstantial direction, whereby liquid is moved from the second container 50 to the first container 40.

As shown in FIG. 6, the second tube 80 links the first container 40 and the second container 50 liquidtightly. No pump is disposed over the second tube 80.

Since the second tube 80 is provided in the above-described manner, when liquid has been moved from the second container 50 to the first container 40 by the tube pump 70 and the liquid height in the first container 40 becomes larger than that of the second container 50, liquid is moved from the first container 40 to the second container 50 through the second tube 80. As a result, the liquid height of the first container 40 can continue to be kept the same as that of the second container 50.

Next, a method for using the tension measuring device 1 according to the embodiment will be described.

First, the first container 40 and the second container 50 are linked to each other by the first tube 60 and the second tube 80 and the tube pump 70 is disposed over the first tube 60. The gel adaptor holder assembly 10 in which a gel G and a cell structure CS are set is set in the first container 40. At this time, for example, a culture medium of 45 ml and a culture medium of 5 ml are put into the first container 40 and the second container 50, respectively.

Then the liquid is caused to circulate through the first container 40 and the second container 50 by the tube pump 70 and the second tube 80. In this state, a medical agent of 5 μl, for example, is input to the second container 50 at a desired timing.

In this state, the tube pump 70 moves liquid from the second container 50 to the first container 40. As a result, the amount of liquid existing in the second container 50 decreases and the amount of liquid existing in the first container 40 increases. Liquid is thus moved from the first container 40 to the second container 50 through the second tube 80 so that the first container 40 and the second container 50 are made the same in liquid height.

As described above, the tension measuring device 1 according to the embodiment is a tension measuring device 1 for a cell structure CS including muscle cells. The tension measuring device 1 has the first container 40 in which the cell structure CS is disposed and which is charged with a culture medium so that the cell structure CS is immersed therein; the second container 50 in which a medical agent to be given to the inside of the first container 40 is injected; the first tube 60 which links the first container 40 and the second container 50 liquidtightly; and the pump 70 which is disposed over the first tube 60 and causes liquid to flow into the first container 40 from the second container 50. In the thus-configured tension measuring device 1, liquid and culture medium are caused to flow into the first container 40 from the second container 50 through the first tube 60 by the pump 70. Thus, vibration that affects the tension detecting means 20 can be made weaker than in a case that the medical agent is caused to flow into the first container 40 directly. As a result, tension can be measured accurately by reducing vibration that affects the tension detecting means 20.

Furthermore, since the tube pump 70 is disposed over the first tube 60 at a position that is spaced from the first container 40, a problem that the tension measurement accuracy is lowered by vibration of the tube pump 70 can be suppressed properly.

Where a chemical is given directly to the inside of the first container 40, the medical agent is administered to the vicinity of the cell structure CS including muscle cells and hence the cell structure CS may be exposed to a high concentration of the medical agent suddenly. In contrast, according to the tension measuring device 1 of the embodiment, the event that the cell structure CS is exposed to a high concentration of the medical agent suddenly can be prevented because the medical agent that has been diluted by culture medium in the second container 50 is given to the inside of the first container 40.

The tension measuring device 1 can further include the second tube 80 which is of a different system than the first tube 60 and links the first container 40 and the second container 50 liquidtightly. With this configuration, liquid can be moved from the first container 40 to the second container 50 without rotating the tube pump 70 in the reverse direction. This makes it possible to circulate liquid through the first container 40 and the second container 50 easily.

The first tube 60 is connected to the first container 40 at a position that is offset from the center line L1 when the first container 40 is seen from above in the vertical direction. With this structure, stirring can be made by generating a rotational flow F in the first container 40. Thus, the medical agent can be mixed with the culture medium faster. Furthermore, an oxygen concentration gradient (the oxygen concentration is higher in a top portion of the first container 40) can be flattened.

The first tube 60 branches into two tubes in the vertical direction at a position where it is connected to the first container 40. With this structure, the medical agent can be mixed faster while the flow speed of liquid flowing into the first container 40 is lowered than with a structure that a single first tube 60 is connected to the first container 40 without branching into two tubes in the vertical direction.

The second container 50 is smaller in surface area than the first container 40. With this structure, the medical agent and the culture medium can be sent from the second container 50 to the first container 40 using small amounts of them.

Embodiment 2

Next, a second embodiment of the presently disclosed subject matter will be described with reference to FIG. 7. The description of features having the same ones in the first embodiment will be omitted and features that are specific to only the second embodiment will be described.

Figure 7:
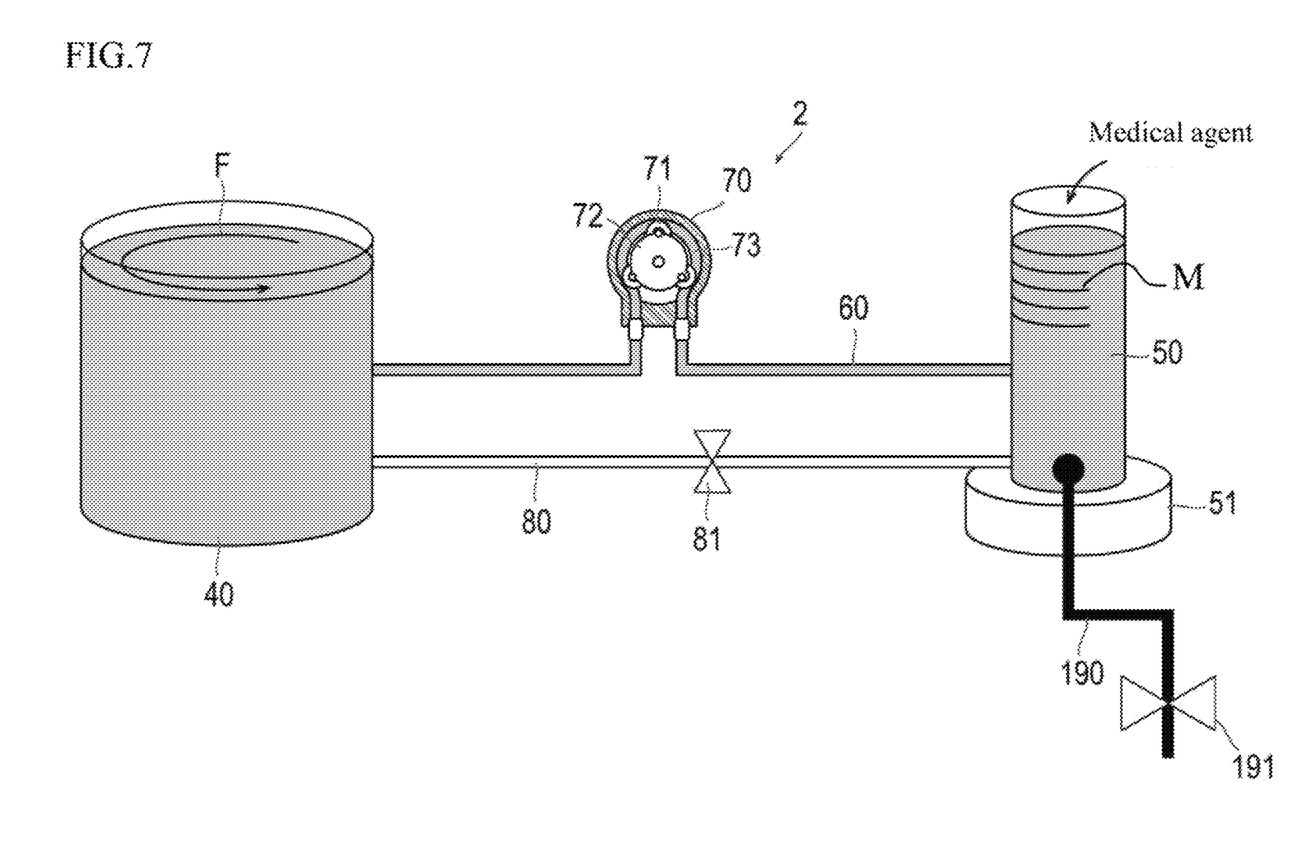
FIG. 7 is a rough diagram of part of a tension measuring device according to a second embodiment of the presently disclosed subject matter.

FIG. 7 is a rough diagram of part of a tension measuring device 2 according to the second embodiment of the presently disclosed subject matter.

As shown in FIG. 7, the tension measuring device 2 according to the second embodiment is different in that, for example, the second container 50 is marked with a scale M, a third tube 190 is connected to the second container 50, and the second tube 80 is provided with an on-off valve 81.

As shown in FIG. 7, in the tension measuring device 2 according to the second embodiment, the second container 50 is marked with the scale M. There are no particular limitations on the intervals between the lines of the scale M; for example, the intervals in the vertical direction are set at 1 mm.

The on-off valve 81 is provided in the second tube 80. The on-off valve 81 is always open during a tension measurement.

The third tube 190 is connected to the second container 50 liquidtightly. An on-off valve 191 is provided in the third tube 190.

The third tube 190 is a tube for disposal. In the tension measuring device 2 according to the second embodiment, the culture medium in each of the first container 40 and the second container 50 can be replaced by opening the on-off valve 191. A fresh culture medium can be input to the first container 40 from the second container 50 by inputting a fresh culture medium to the second container 50 and driving the tube pump 70.

The tension measuring device 2 is required to keep the amount of culture medium in the first container 40 constant by inputting culture medium by the same amount as an evaporation amount when culture medium has evaporated from the first container 40.

In the tension measuring device 2 according to the second embodiment, the on-off valve 81 provided in the second tube 80 is closed when culture medium has evaporated from the first container 40. Liquid is then supplied from the second container 50 to the first container 40 by the tube pump 70 so that liquid of 45 ml comes to exist in the first container 40. The amount of culture medium existing in the first container 40 can be kept constant by inputting culture medium to the second container 50 by recognizing a liquid decrease in the second container 50 using the scale M. A decrease of culture medium in the first container 40 can be recognized properly using the second container 50 because the second container 50 is smaller in surface area than the first container 40.

When culture medium has evaporated from the first container 40, a liquid decrease in the second container 50 that occurs when the height of the first container 40 is lowered so that liquid of 45 ml comes to be contained therein may be recognized using the scale M.

Embodiment 3

Next, a third embodiment of the presently disclosed subject matter will be described with reference to FIG. 8. The description of features having the same ones in the first embodiment will be omitted and features that are specific to only the third embodiment will be described.

Figure 8:
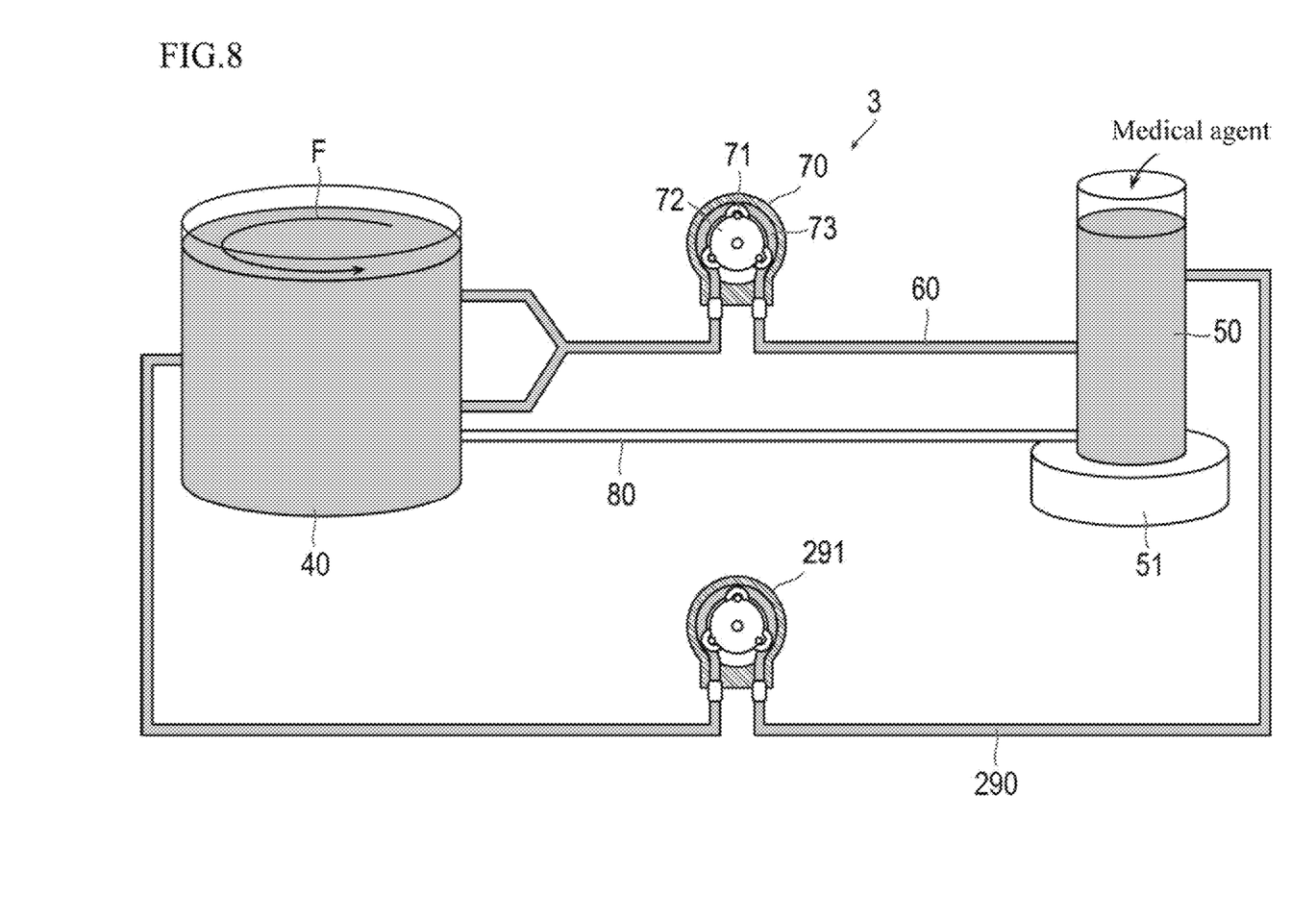
FIG. 8 is a rough diagram of part of a tension measuring device according to a third embodiment of the presently disclosed subject matter.

FIG. 8 is a rough diagram of part of a tension measuring device 3 according to the third embodiment of the presently disclosed subject matter.

As shown in FIG. 8, the tension measuring device 3 according to the third embodiment is different in that a fourth tube 290 is provided so as to be of a different system than the first tube 60 and the second tube 80.

The tension measuring device 3 according to the third embodiment can include the fourth tube 290 which links the first container 40 and the second container 50 liquidtightly. A tube pump 291 (which corresponds to an inflow pump) is provided in the fourth tube 290.

The tube pump 291 moves liquid from the first container 40 to the second container 50. Liquid is circulated through the first container 40 and the second container 50 by moving liquid from the second container 50 to the first container 40 by the tube pump 70 and moving liquid from the first container 40 to the second container 50 by the tube pump 291.

Even if the tube pump 70 and the tube pump 291 produce different flow speeds, the second tube 80 can make the first container 40 and the second container 50 be the same in liquid height.

The presently disclosed subject matter is not limited to the above-described embodiments and various modifications are possible within the confines of the claims.

For example, in the above-described first embodiment, the heater 51 is disposed under the second container 50. Alternatively, a structure is possible in which a heater is disposed on the outer circumferential surface of the first tube 60 or the second tube 80.

In the above-described first embodiment, the tension measuring device 1 has the second tube 80. Alternatively, the second tube 80 may be omitted from the tension measuring device 1. In this case, liquid is reciprocated between the first container 40 and the second container 50 by rotating the tube pump 70 in the normal direction and the reverse direction.

In the above-described first embodiment, the first tube 60 is connected to the first container 40 at the position that is offset from the center line L1. Alternatively, where, for example, a gel G and a cell structure CS that are held by the gel adaptor holder assembly 10 are offset from the center line L1 that passes through the center of the first container 40 and is perpendicular to the first container 40 which extends in the vertical direction, the first tube may be connected to the first container 40 at a position that is not offset from the center line L1.

In the above-described first embodiment, the first tube 60 branches into two tubes in the vertical direction at the position where it is connected to the first container 40. Alternatively, where, for example, the flow speed in the tube is high because, for example, the tube inner diameter is small, the first tube 60 may branch into three or more tubes. As a further alternative, the first tube 60 may branch at the position where it is connected to the first container 40 in a direction that is not the vertical direction, such as the top-bottom direction or the left-right direction. Furthermore, the first tube 60 need not always branch at the position where it is connected to the first container 40.

In the above-described first embodiment, the second container 50 is smaller in surface area than the first container 40. Alternatively, the second container may be configured so as to be larger than or equal to the first container 40 in surface area.

In the above-described first embodiment, the tube pump 70 which is disposed over the first tube 60 is configured so as to have the three rollers 71 which are arranged in the circumferential direction at intervals of 120°. However, the number of rollers 71 is not limited to three and may be larger than or smaller than three.

In the second embodiment, the second container 50 is marked with the scale M. However, what is marked with a scale M is not limited to the second container 50; the first container 40 may be marked with a scale M. In this case, there are no particular limitations on the intervals between the lines of the scale M; for example, the lines may be formed at intervals of 1 mm in the vertical direction.

What is claimed is:

1. A tension measuring device, comprising:
    a holder that holds a cell structure including muscle cells;
    a first container including a culture medium and the holder, the cell structure being immersed in the culture medium;
    a second container including a medical agent;
    a first tube which links the first container and the second container liquidtightly;
    a pump which is disposed over the first tube and causes liquid to flow into the first container from the second container; and
    a load cell linked to the holder and configured to measure a tension of the cell structure including muscle cells,
    wherein the first tube is connected to a lateral surface of the first container at a position entirely immersed in the culture medium, and
    wherein the first tube is connected to the first container at a position that is offset from a center line when the first container is seen from above in a vertical direction.

2. The tension measuring device according to claim 1, further comprising a second tube which links the first container and the second container liquidtightly.

3. A tension measuring device, comprising:
    a holder that holds a cell structure including muscle cells;
    a first container including a culture medium and the holder, the cell structure being immersed in the culture medium;
    a second container including a medical agent;
    a first tube which links the first container and the second container liquidtightly;
    a pump which is disposed over the first tube and causes liquid to flow into the first container from the second container; and
    a load cell linked to the holder and configured to measure a tension of the cell structure including muscle cells,
    wherein the first tube is connected to a lateral surface of the first container,
    wherein the first tube is connected to the first container at a position that is offset from a center line when the first container is seen from above in a vertical direction,
    wherein the first tube branches into plural tubes in a vertical direction at a position where the first tube is connected to the first container.

4. The tension measuring device according to claim 1, wherein the second container is smaller in surface area than the first container.

5. The tension measuring device according to claim 1, wherein the second container is marked with a scale which indicates a residual amount of liquid.

6. The tension measuring device according to claim 1, further comprising a second tube which is connected to the second container and serves to discard a liquid existing in the second container.

7. A tension measuring device, comprising:
    a holder that holds a cell structure including muscle cells;
    a first container including a culture medium and the holder, the cell structure being immersed in the culture medium;
    a second container including a medical agent;
    a first tube which links the first container and the second container liquidtightly;
    a pump which is disposed over the first tube and causes liquid to flow into the first container from the second container;
    a load cell linked to the holder and configured to measure a tension of the cell structure including muscle cells;
    a second tube which links the first container and the second container liquidtightly; and
    an inflow pump which is disposed over the second tube and causes liquid to flow into the second container from the first container, wherein the first tube is connected to a lateral surface of the first container, and wherein the first tube is connected to the first container at a position that is offset from a center line when the first container is seen from above in a vertical direction.

8. The tension measuring device according to claim 1, wherein the pump is a tube pump disposed over the first tube.

9. The tension measuring device of claim 1, wherein the cell structure including muscle cells comprises a sheet cell structure, a rod cell structure, or a string cell structure.

10. The tension measuring device of claim 1, wherein the holder is fixed to a lid of the first container, and the lateral surface of the first container is different from the lid of the first container.

11. The tension measuring device of claim 10, wherein the first tube is connected directly to the lateral surface of the first container.

* * * * *